United States Patent
Amundson et al.

(10) Patent No.: US 8,938,866 B2
(45) Date of Patent: Jan. 27, 2015

(54) INTEGRATED TAMPON AND METHOD FOR MAKING

(75) Inventors: John David Amundson, Greenville, WI (US); Mary Lou McDaniel, Appleton, WI (US); Lars Nilsen Nordang, Neenah, WI (US); Charles Robert Tomsovic, Omro, WI (US); Melissa Kay Burns, Flint, MI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 614 days.

(21) Appl. No.: 13/100,066

(22) Filed: May 3, 2011

(65) Prior Publication Data
US 2012/0283685 A1    Nov. 8, 2012

(51) Int. Cl.
*A61F 13/20*    (2006.01)

(52) U.S. Cl.
CPC ......... *A61F 13/2031* (2013.01); *A61F 13/2088* (2013.01)
USPC .......................................................... 28/118

(58) Field of Classification Search
CPC .................... A61F 13/2031; A61F 13/2088
USPC .......... 28/118, 119, 120; 604/385.17, 385.18, 604/904
See application file for complete search history.

(56) References Cited

U.S. PATENT DOCUMENTS

| | | | |
|---|---|---|---|
| 2,123,750 A * | 7/1938 | Schulz | ........................... 604/365 |
| 2,499,414 A | 3/1950 | Rabell | |
| 3,610,243 A | 10/1971 | Jones, Sr. | |
| 3,624,746 A | 11/1971 | Grad et al. | |
| 4,175,561 A * | 11/1979 | Hirschman | .............. 604/385.17 |
| 4,373,529 A | 2/1983 | Lilaonitkul et al. | |
| 4,787,895 A | 11/1988 | Stokes et al. | |
| 5,047,024 A | 9/1991 | Glassman | |
| 5,165,152 A * | 11/1992 | Kramer et al. | .................. 28/118 |
| 6,758,839 B2 | 7/2004 | Lochte et al. | |
| 7,059,026 B2 * | 6/2006 | Friese et al. | .................... 28/118 |
| 7,735,203 B2 | 6/2010 | Stan et al. | |
| 7,977,532 B2 | 7/2011 | Hasse et al. | |
| 2002/0133135 A1 | 9/2002 | Gell et al. | |
| 2002/0151859 A1 * | 10/2002 | Schoelling | .............. 604/385.17 |
| 2004/0030316 A1 * | 2/2004 | Gubernick et al. | ........... 604/383 |
| 2004/0193131 A1 | 9/2004 | Wada | |
| 2004/0226152 A1 * | 11/2004 | Prosise et al. | .................... 28/118 |
| 2005/0113780 A1 * | 5/2005 | Gatto et al. | ............. 604/385.17 |
| 2005/0113783 A1 * | 5/2005 | Carlin et al. | ............. 604/385.18 |
| 2005/0113807 A1 | 5/2005 | Carlin | |
| 2005/0143708 A1 * | 6/2005 | Hagberg et al. | .......... 604/385.18 |
| 2005/0177090 A1 | 8/2005 | Jensen | |
| 2007/0083182 A1 | 4/2007 | Schoelling | |
| 2008/0064581 A1 | 3/2008 | Lochte et al. | |

(Continued)

FOREIGN PATENT DOCUMENTS

CN          101541280 A      9/2009
DE      102005050514 A1      4/2007

(Continued)

*Primary Examiner* — Amy Vanatta
(74) *Attorney, Agent, or Firm* — Kimberly-Clark Worldwide, Inc.

(57) ABSTRACT

A method of integrating a tampon includes providing an absorbent blank having a longitudinal centerline and compressing the absorbent blank in a direction perpendicular to the longitudinal centerline to form a pledget having a compressed diameter. The method also includes penetrating the pledget in the perpendicular direction to a compressed depth of at least 20% of the compressed diameter to form a discrete indentation.

9 Claims, 18 Drawing Sheets

(56) References Cited

U.S. PATENT DOCUMENTS

| | | |
|---|---|---|
| 2008/0154222 A1* | 6/2008 | Chaffringeon ................ 604/361 |
| 2009/0082712 A1 | 3/2009 | Hasse et al. |
| 2011/0092940 A1 | 4/2011 | Fung et al. |
| 2011/0230854 A1 | 9/2011 | Smet |
| 2011/0238028 A1* | 9/2011 | Smet ........................ 604/385.17 |
| 2012/0010587 A1* | 1/2012 | Smet ............................. 604/379 |
| 2012/0089111 A1* | 4/2012 | Magnusson et al. ..... 604/385.18 |
| 2012/0137479 A1* | 6/2012 | Rolli et al. ...................... 28/118 |
| 2013/0110074 A1* | 5/2013 | Smet et al. ............... 604/385.17 |

FOREIGN PATENT DOCUMENTS

| | | |
|---|---|---|
| EP | 1 459 720 B1 | 4/2005 |
| EP | 2 404 584 A1 | 1/2012 |
| WO | WO 2011/000507 A1 | 1/2011 |
| WO | WO 2011/002357 A1 * | 1/2011 |

* cited by examiner

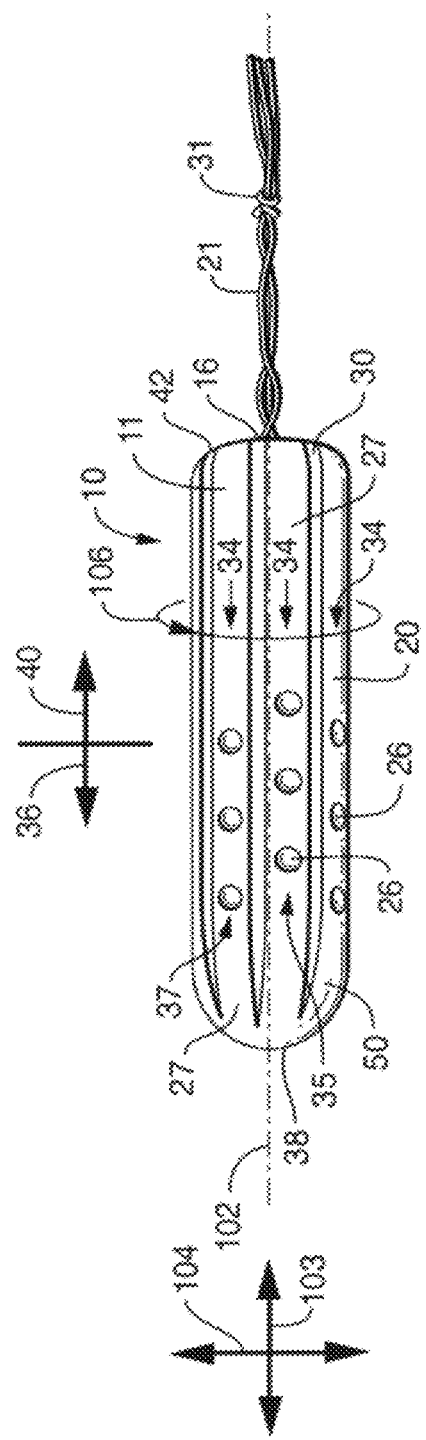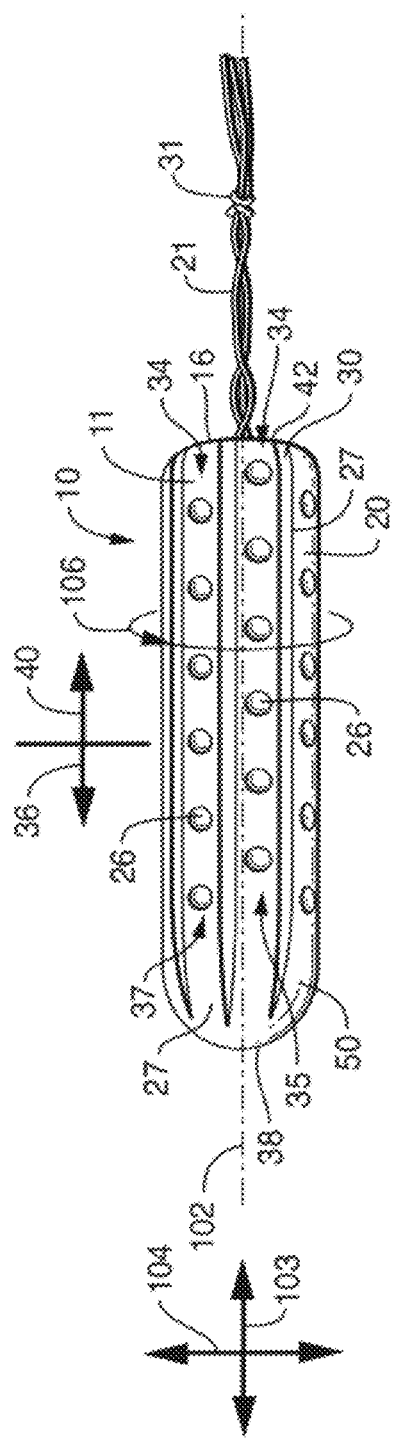

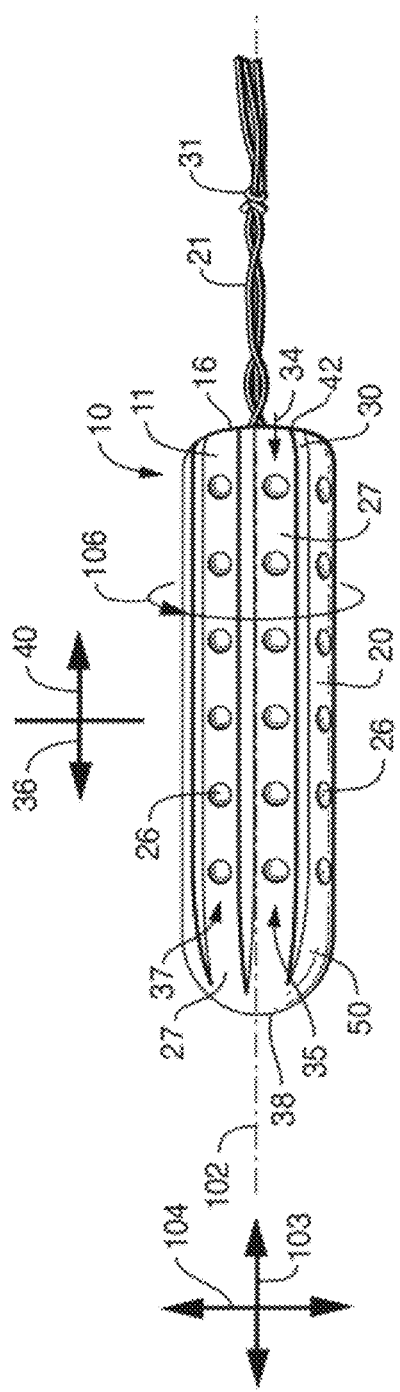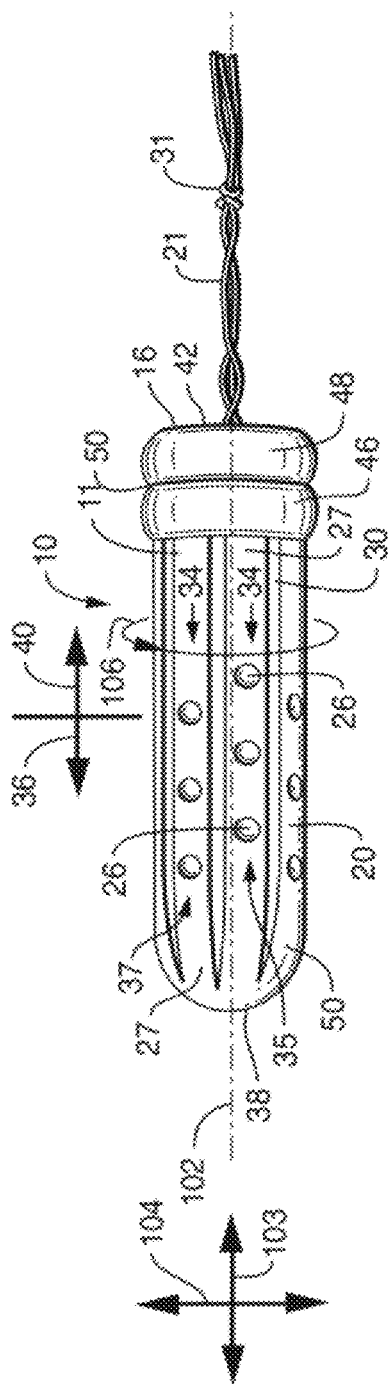

INTEGRATED TAMPON AND METHOD FOR MAKING

BACKGROUND OF THE INVENTION

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding, rolling, or stacking a loosely associated rectangular strip of absorbent material into a blank and then compressing the blank into a cylindrically-shaped product known as a pledget. The pledget may or may not have a cover. In both types, a withdrawal string is attached to the pledget before the tampon is wrapped and packaged for sale. In the applicator style tampon, the tampons are assembled into an applicator prior to being wrapped and packaged.

In use, tampons are designed to be inserted into a woman's vagina to intercept the fluid flow of menses, blood, and other body fluids and to prevent the fluid from exiting the vagina. When the user is ready to remove the tampon from the vagina, she pulls on the withdrawal string connected to the tampon. Ideally, the used tampon remains fully intact as it is withdrawn and does not substantially delaminate, unroll, unfold, telescope, or otherwise structurally degrade. However, this ideal is not always achieved due to various factors such as saturation level, withdrawal angle, wear time, and numerous other factors. To combat these structural issues, numerous attempts to stabilize the tampons have been undertaken. For example, some have tried binder fibers, adhesives, grooved compression, needling, microwave radiation, and the like. However, despite these efforts, there still exists a need for tampons having greater pledget stability during use and during withdrawal.

SUMMARY OF THE INVENTION

In one aspect, the present invention provides a method of integrating a tampon. The method includes providing an absorbent blank having a longitudinal centerline and compressing the absorbent blank in a direction perpendicular to the longitudinal centerline to form a pledget having a compressed diameter. The method also includes penetrating the pledget in the perpendicular direction to a compressed depth of at least 20% of the compressed diameter to form a discrete indentation.

In some embodiments, the discrete indentation has a displaced volume at peak compression of at least 5 cubic millimeters.

In some embodiments, the compressing step and the penetrating step are performed in a single compression unit.

In some embodiments, the method further includes the step of compressing a plurality of longitudinal grooves in the pledget during the compressing step.

In some embodiments, the method includes the step of at least partially wrapping the absorbent blank with a cover before compressing the absorbent blank and the cover to form the pledget. In these embodiments, the method may also include penetrating the pledget and the cover in the perpendicular direction to a compressed depth of at least 30% of the compressed diameter to form the discrete indentation.

In some embodiments, the pledget defines a first half having an insertion end and a second half having a withdrawal end and the method further includes penetrating the pledget in the perpendicular direction to form 25% more indentations in the first half than the second half.

In some embodiments, the method further includes the step of forming a first circumferentially raised ring around the pledget in the second half. In some embodiments, the method further includes the step of forming a second circumferentially raised ring around the pledget wherein the first circumferentially raised ring and the second circumferentially raised ring are separated by a circumferential groove.

In some embodiments, the method includes penetrating the pledget in the perpendicular direction to form a plurality of longitudinal rows of indentations wherein a first row of indentations is staggered in the circumferential direction as compared with a second adjacent row of indentations.

In another aspect, the present invention provides another method of integrating a tampon. The method includes providing an absorbent blank with a longitudinal centerline and compressing the absorbent blank into a pledget having a compressed diameter and a plurality of longitudinal grooves. The method also includes penetrating the pledget in a direction perpendicular to the longitudinal centerline to form a plurality of longitudinal rows of indentations wherein the longitudinal grooves and the longitudinal rows of indentations are circumferentially alternating.

In some embodiments, the pledget is penetrated to a compressed depth of at least 30% of the compressed diameter.

In some embodiments, the rows of indentations and the rows of grooves are formed in a single compression unit.

In some embodiments, a first row of indentations is staggered in a circumferential direction as compared with a second row of indentations.

In some embodiments, the pledget defines a first half and a second half and the method further includes forming more indentations in the first half than in the second half.

In another aspect, the present invention provides an integrated tampon. The integrated tampon includes an absorbent pledget and a withdrawal string. The absorbent pledget defines a longitudinal direction, a circumferential direction, a first half, and a second half. The withdrawal string extends from the second half. The absorbent pledget has a plurality of longitudinal grooves and a plurality of longitudinal rows of indentations alternating in the circumferential direction.

In some embodiments, the first half has 25% more indentations than the second half.

In some embodiments, a first row of indentations is staggered in the circumferential direction as compared with a second row of indentations.

In some embodiments, the tampon also includes a cover material and the indentations include a first void space above the cover material and a second void space below the cover material.

In some embodiments, the tampon includes a first circumferentially raised ring around the pledget in the second half. In some embodiments, the tampon includes a second circumferentially raised ring around the pledget. The first circumferentially raised ring and the second circumferentially raised ring are separated by a circumferential groove.

BRIEF DESCRIPTION OF THE DRAWINGS

FIGS. 1-4 representatively illustrate exemplary tampons of the present invention.

DETAILED DESCRIPTION OF THE DRAWINGS

Figure 5:
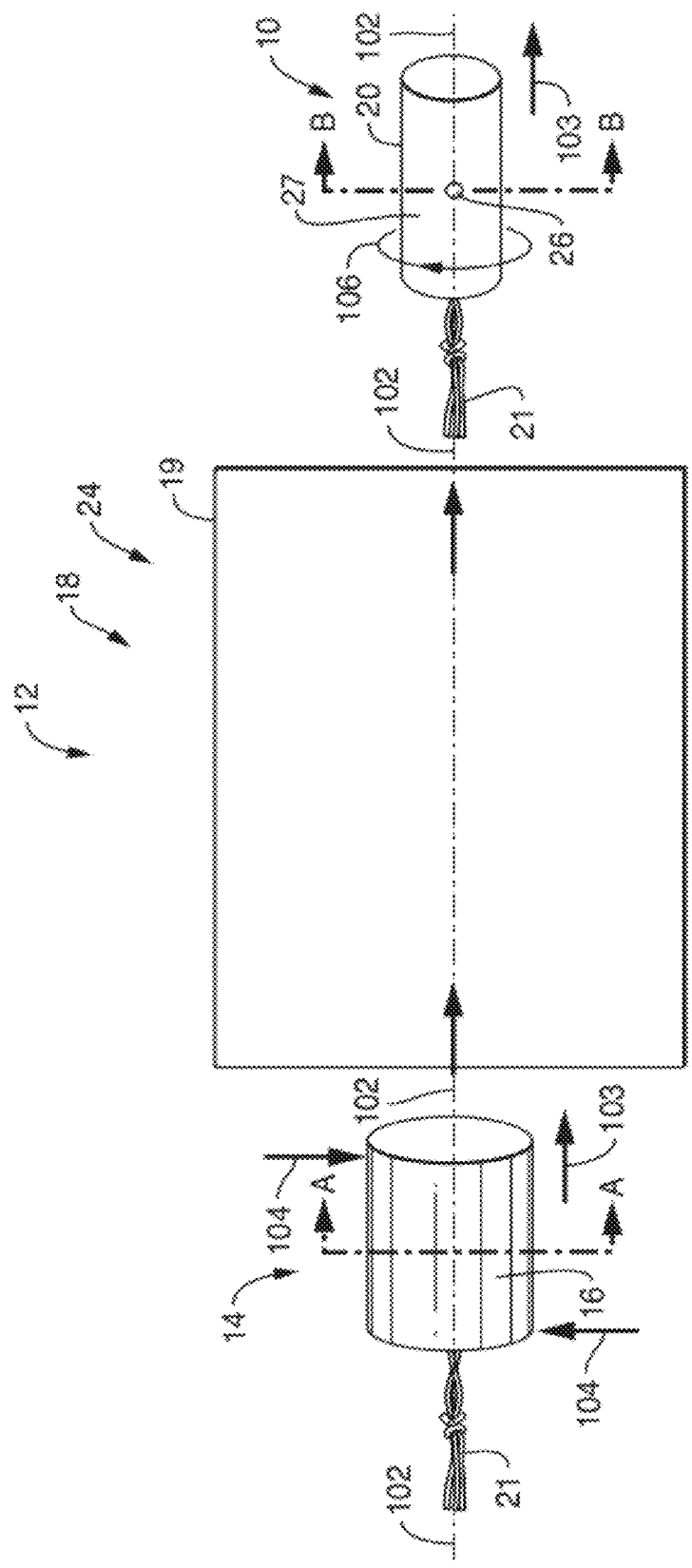
FIG. 5 representatively illustrates an exemplary method of the present invention.

The tampon of the present invention is designed to be inserted above the introital region of a woman's vagina and is designed to function so as to intercept the fluid flow of menses, blood, and other body fluids and prevent the fluid from exiting the vagina. While the pledgets of the present invention are described for use as a menstrual device, it will be readily apparent that the pledgets may also be used as any other suitable vaginal insert, such as a pessary. Likewise, while the pledgets of the present invention are generally described as being "absorbent", it will be readily apparent that the pledgets may be coated or otherwise treated to be partially or completely non-absorbent.

As is shown in FIGS. 1-4, exemplary tampons 10 include a mass of fibrous material 11 compressed into a generally cylindrically-shaped pledget 20 having a longitudinal centerline 102. The tampon 10 generally has an insertion end 38 and an opposite withdrawal end 42. The insertion end 38 is designed to be the first part of the tampon which enters the woman's vaginal cavity. In some embodiments, the insertion end 38 may be rounded or otherwise shaped to facilitate insertion. While in use, the pledget 20 of the present invention is designed to be entirely positioned within the woman's vagina.

The tampon 10 further includes a withdrawal string 21 for assisting in removing the tampon 10 from the woman's vagina. The withdrawal string 21 may be attached to the pledget 20 in any suitable manner. The withdrawal string 21 may further include one or more knots 31 to prevent fraying of the withdrawal string 21 and to provide a point where a woman can grasp the withdrawal string 21 when she is ready to remove the tampon 10 from her vagina.

When the woman pulls on the withdrawal string 21, forces are applied to the connection points between the withdrawal string 21 and the pledget 20. These forces are counteracted by the frictional forces between the pledget 20 and the vaginal walls. The frictional forces vary depending upon the saturation level of the pledget, the presence and/or type of cover material, pledget expansion, pledget orientation, the rheology of the body fluids present, and numerous other factors. Regardless of the various factors, it is desirable that the integrity of the pledget be such that it can withstand the countervailing forces without delaminating, unrolling, unfolding, telescoping, or otherwise structurally degrading. While not wishing to be bound by theory, it is believed that these and other structural degradations are caused, at least in part, by shifting between various layers or structures of the pledget. These shifts are believed to be compounded by the fact that the pledgets are generally made from ribbons of fiber that may be wound, folded, stacked, gathered, bunched, waded, bagged, or the like. Past efforts to stabilize the pledget have included the use of binder fibers, adhesives, grooved compression, needling, microwave radiation, and the like in an effort to achieve fiber to fiber stability. While these methods have had mixed success, the present invention is believed to increase layer or structure integration by mechanically driving discrete portions of outer layers or structures into adjacent inner layers or structures.

Figure 6:
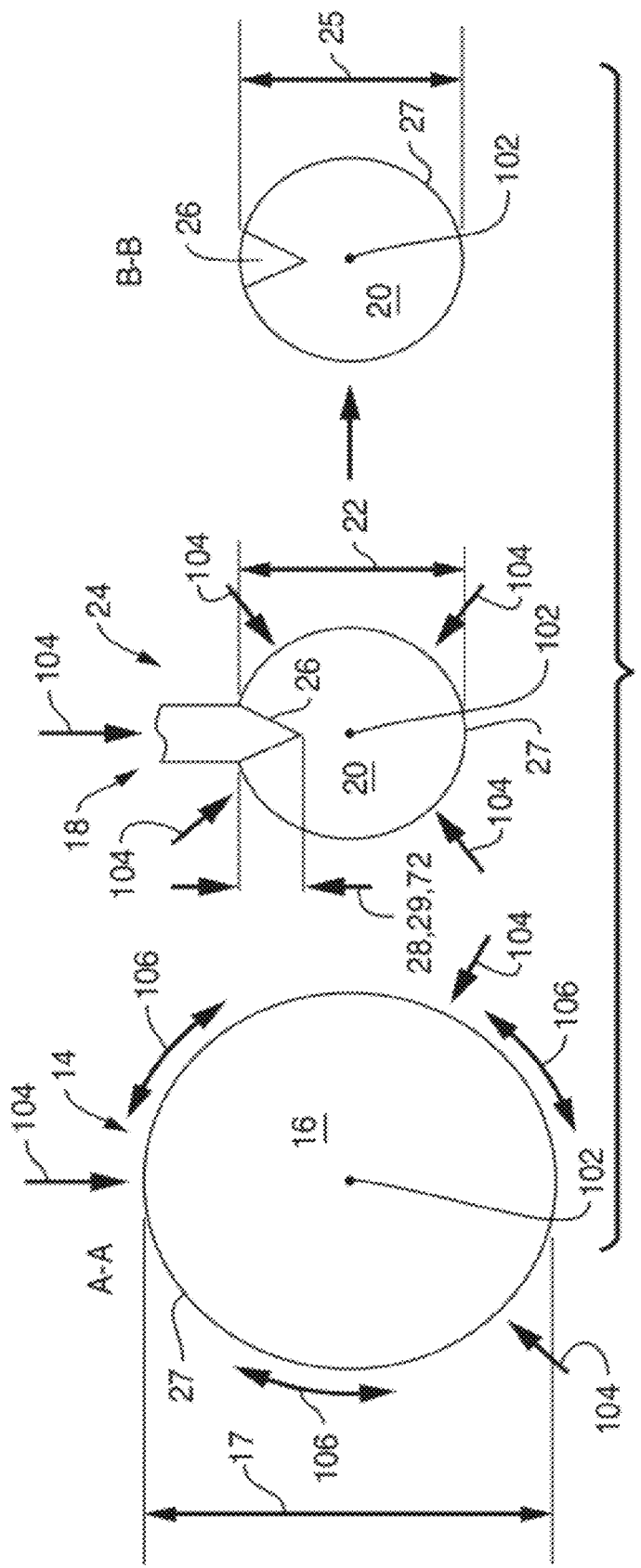
FIG. 6 representatively illustrates various cross-sectional views at different points in the method of FIG. 5.

Thus, the present invention includes a method for making a tampon having increased layer or structure integration. Referring now to FIG. 5, an exemplary method 12 for making a tampon 10 having improved layer integration is illustrated. The method 12 includes a step 14 of providing an absorbent blank 16. The absorbent blank 16 has an initial diameter 17 (FIG. 6) before being inserted into a compression unit 19. Within the compression unit 19, the method 12 includes a step 18 of compressing the absorbent blank 16 in a direction 104. The direction 104 is perpendicular to and radially inward towards the longitudinal center line 102. The absorbent blank 16 is compressed from the initial diameter 17 to a compressed diameter 22 (FIG. 6). The method 12 also includes a step 24 of penetrating the pledget 20, when at the compressed diameter 22, in the direction 104 to form a discrete indentation 26 having an indentation depth 28 (FIG. 6).

Referring now to FIG. 6, a cross-sectional view of the absorbent blank 16 taken along line A-A of FIG. 5 is representatively illustrated. As illustrated, the absorbent blank 16 has an initial diameter 17 when provided (step 14) to the compression unit 19. The absorbent blank 16 defines multiple directions 104 that are perpendicular to and radially inward towards the longitudinal center line 102. The absorbent blank 16 also defines a circumferential direction 106. FIG. 6 also illustrates a cross-sectional view of the absorbent blank 16 at the point of peak compression into the pledget 20 having a compressed diameter 22 (center illustration). The center illustration of FIG. 6 also illustrates the step 24 of penetrating the pledget 20 in the perpendicular direction 104 to form a discrete indentation 26 having a compressed depth 28 of at least 20% of the compressed diameter 22. Finally, FIG. 6 illustrates a cross-sectional view of the pledget 20 taken along line B-B of FIG. 5. In this view, the pledget 20 illustrates a recovered diameter 25 and the discrete indentation 26.

Figure 7:
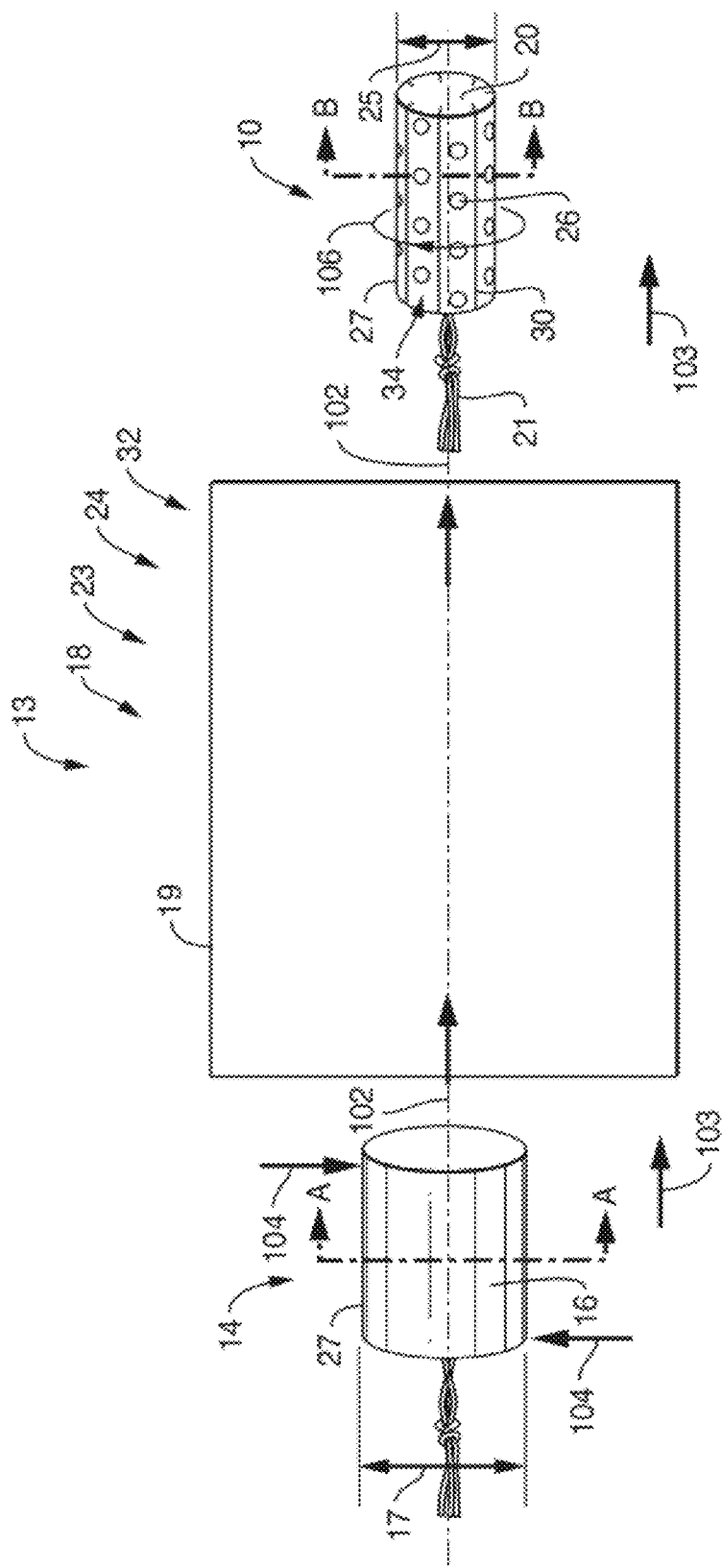
FIG. 7 representatively illustrates another exemplary method of the present invention.

In various embodiments, the compressing step 18 and the penetrating step 24 may be executed sequentially in separate operations. In other embodiments, the compressing step 18 and the penetrating step 24 may be executed in the same compression unit 19 as illustrated in FIGS. 5 and 7. In various embodiments, the steps 18 and 24 may occur simultaneously or in rapid succession within the same compression unit 19.

Figure 8:
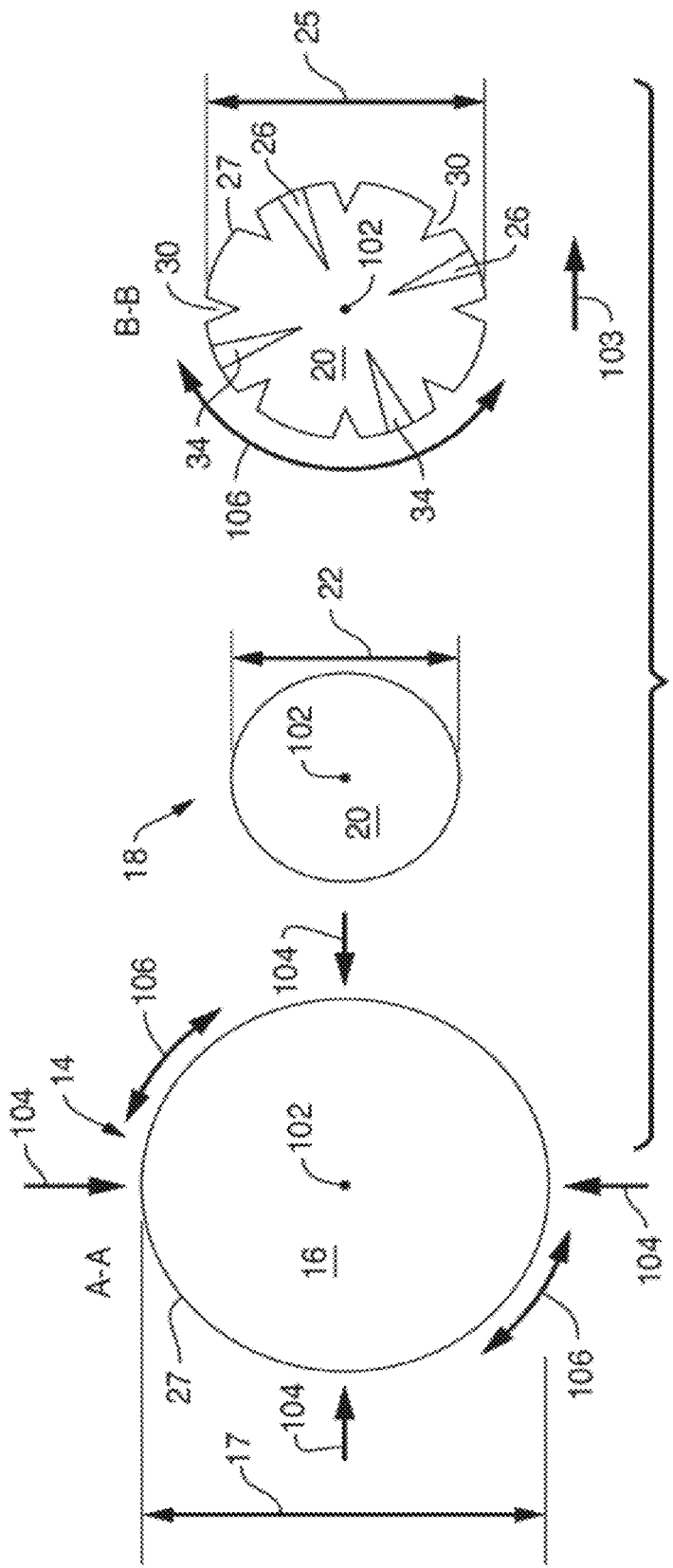
FIG. 8 representatively illustrates various cross-sectional views at different points in the method of FIG. 7.

The present invention also includes another method for making a tampon having increased layer or structure integration. Referring now to FIG. 7, another exemplary method 13 for making a tampon 10 having improved layer or structure integration is illustrated. Also, referring to FIG. 8, various cross-sectional views from FIG. 7 are illustrated. Specifically, FIG. 8 illustrates a cross-sectional view of the absorbent blank 16 taken along line A-A of FIG. 7. FIG. 8 also illustrates a cross-sectional view of the absorbent blank 16 at the peak of compression into pledget 20 (center illustration). Finally, FIG. 8 illustrates a cross-sectional view of the pledget 20 taken along line B-B of FIG. 7. In this view, the pledget 20 illustrates a recovered diameter 25. The method 13 includes a step 14 of providing an absorbent blank 16. The absorbent blank 16 has an initial diameter 17 before being inserted into a compression unit 19. Within the compression unit 19, the method 13 includes a step 18 of compressing the absorbent blank 16 in the perpendicular direction (i.e., radially inward) 104 from the initial diameter 17 into a pledget 20 having a compressed diameter 22. The method 13 may also include a step 23 of forming one or more longitudinal grooves 30. The method 13 also includes a step 24 of penetrating the pledget 20 in the perpendicular direction 104 to form one or more indentations 26. In some embodiments, the method 13 includes forming one or more longitudinal rows 34 of indentations 26. In various embodiments, the method 13 may also include the step of forming a plurality of longitudinal grooves 30 and a plurality of longitudinal rows 34 of indentations 26. In some embodiments, the method 13 may include the step 32 of alternating the longitudinal grooves 30 and the longitudinal rows 34 of indentations 26 in the circumferential direction 106 as illustrated in FIG. 8.

In general, the compression unit 19 may utilize one or more dies which reciprocate relative to one another so as to form a mold cavity there between. When the absorbent blank is positioned within the mold cavity, the dies may be actuated so as to move towards one another and compress the absorbent blank. The absorbent blank may be compressed any suitable amount. For example, the absorbent blank may be compressed to at least 75%, at least 50%, or at least 25% of the initial dimensions. For example, absorbent blanks may be reduced in diameter to approximately ¼ of the initial diameter. In some embodiments, the absorbent blanks may be reduced in diameter from about 28.5 mm to about 6.6 mm, which is approximately 23% of the initial diameter. The cross-sectional configuration of the resultant pledgets 20 may be circular, ovular, rectangular, hexagonal, or any other suitable shape, or combinations thereof. For pledgets 20 having a non-circular cross-section (i.e., non-cylindrical), the term "diameter" refers to the diameter of the largest circle that can be inscribed within the non-circular cross-sectional area.

Figure 9:
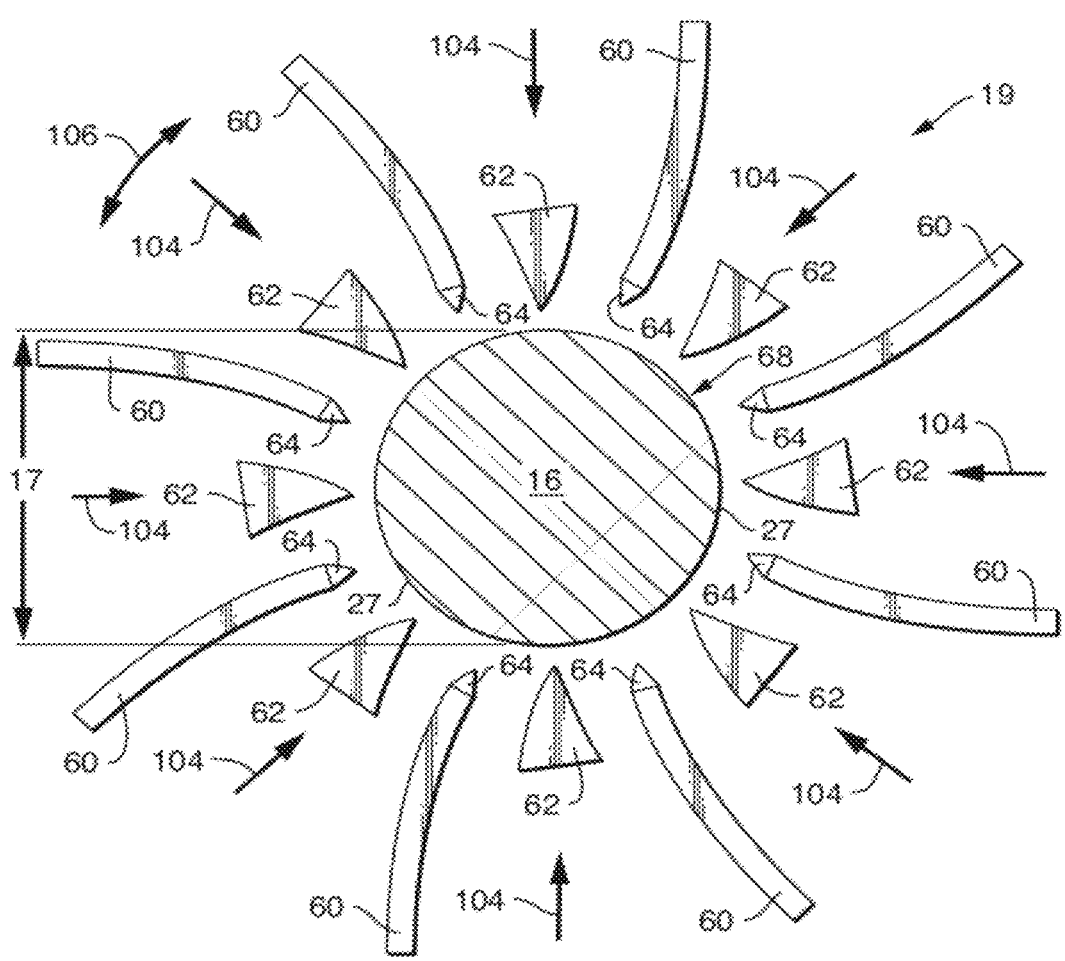
FIG. 9 representatively illustrates an end view of an exemplary compression unit of the present invention in an uncompressed configuration.

Referring now to FIG. 9, an end view of an exemplary absorbent blank 16 is illustrated in an exemplary compression unit 19. The compression unit 19 may include any suitable number of indentation press jaws 60. For example, the compression unit 19 may include 1, 2, 3, 4, 5, 6, 7, 8, 9, or at least 10 indentation press jaws 60. In the embodiment of FIG. 9, eight indentation press jaws 60 are illustrated evenly spaced in the circumferential direction 106 of the absorbent blank 16. In various embodiments, the compression unit 19 may also include any suitable number of groove press jaws 62. For example, the compression unit 19 may include 1, 2, 3, 4, 5, 6, 7, 8, 9, or at least 10 groove press jaws 62. The indentation press jaws 60 and the groove press jaws 62 (if present) collectively define a mold cavity 68. In the embodiment of FIG. 9, eight groove press jaws 62 are illustrated evenly spaced in the circumferential direction 106 of the absorbent blank 16. Additionally, FIG. 9 representatively illustrates the eight indentation press jaws 60 alternately and evenly spaced with the eight groove press jaws 62 in the circumferential direction 106 of the absorbent blank 16. Collectively, the eight indentation press jaws 60 and the eight groove press jaws 62 define the mold cavity 68.

Figure 10:
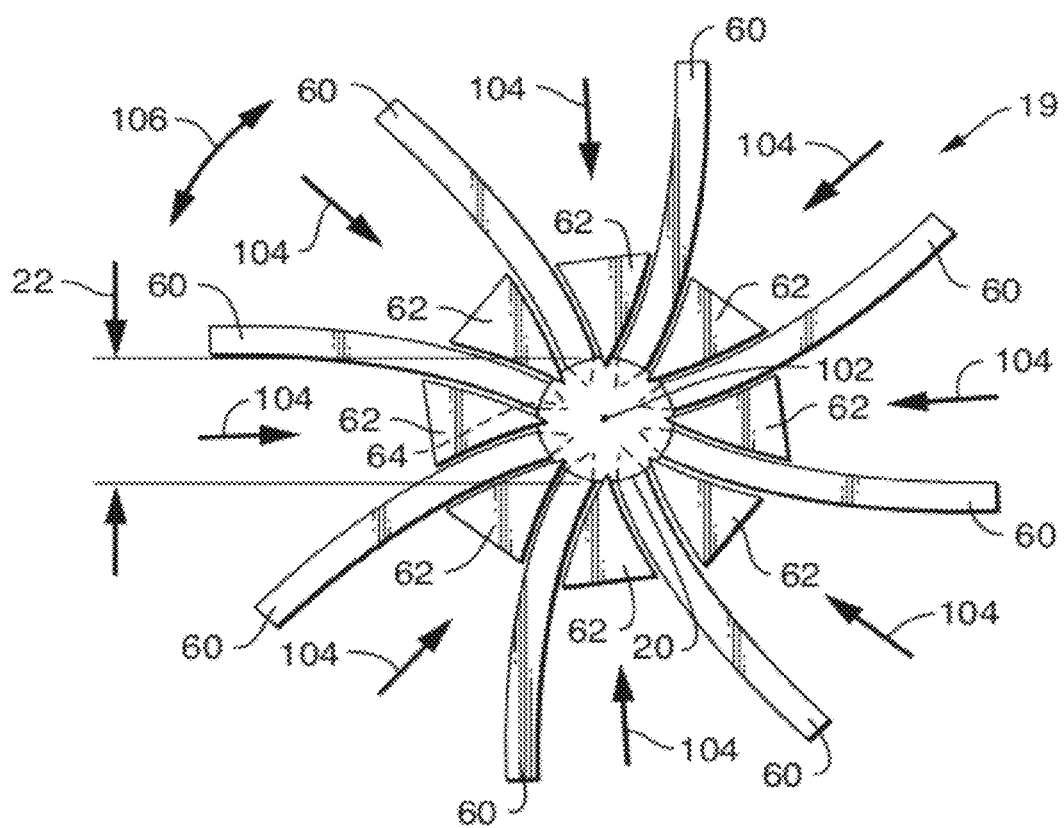
FIG. 10 representatively illustrates an end view of the compression unit of FIG. 9 in a compressed configuration.
Figure 11:
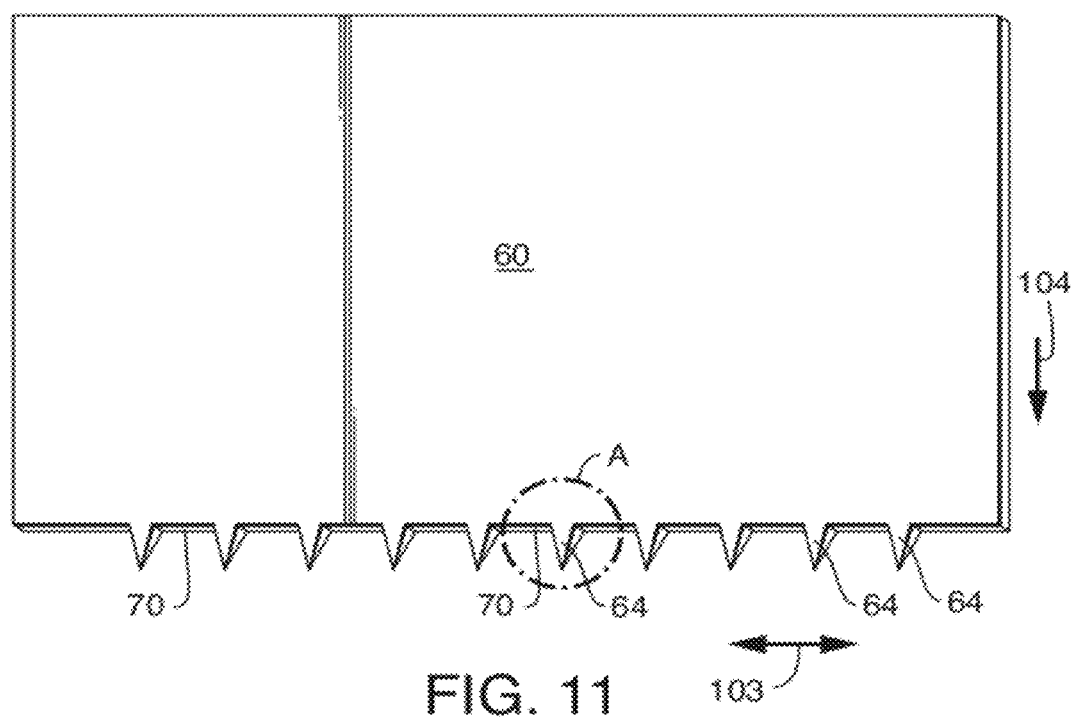
FIG. 11 representatively illustrates a broad side view of an exemplary indentation press jaw of the present invention.
Figure 12:
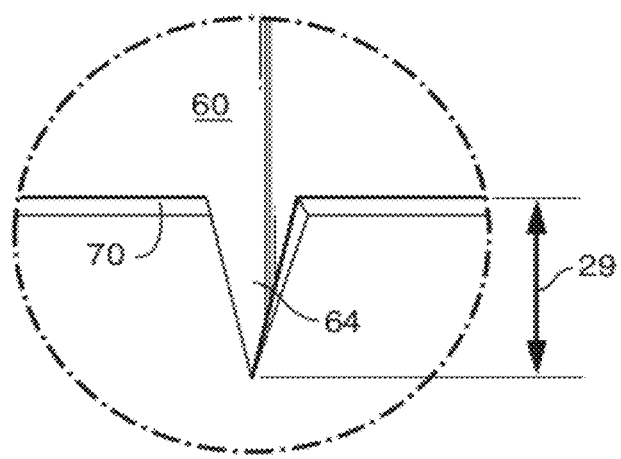
FIG. 12 representatively illustrates an enlarged view of detail A of FIG. 11.
Figure 13:
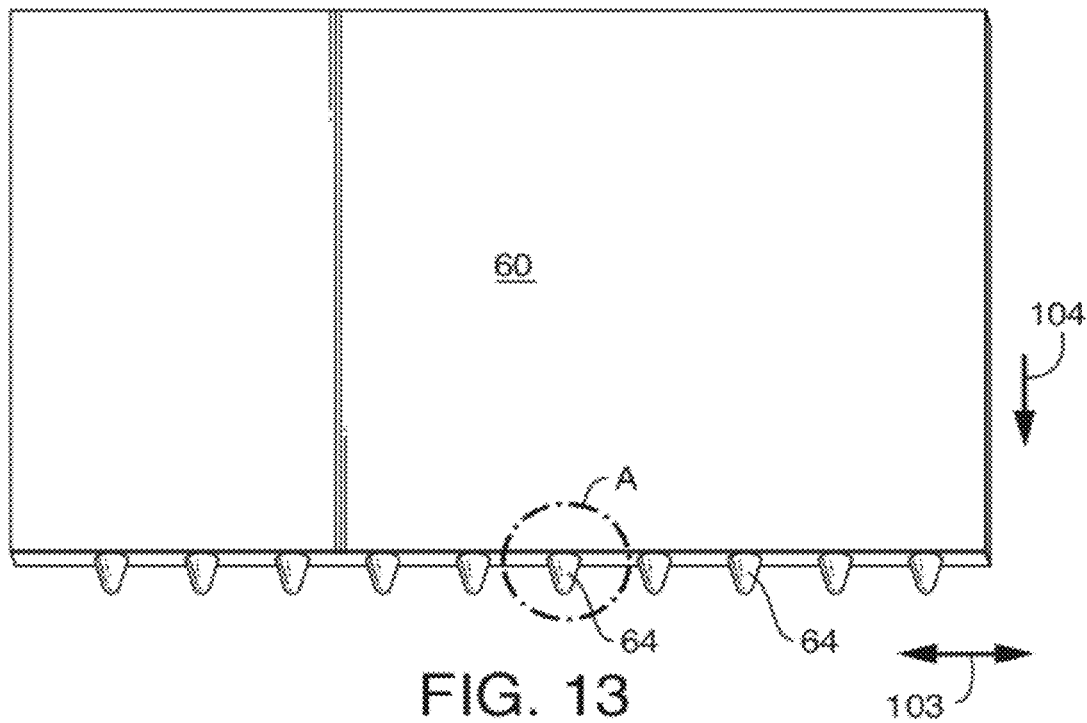
FIG. 13 representatively illustrates a broad side view of another exemplary indentation press jaw of the present invention.
Figure 14:
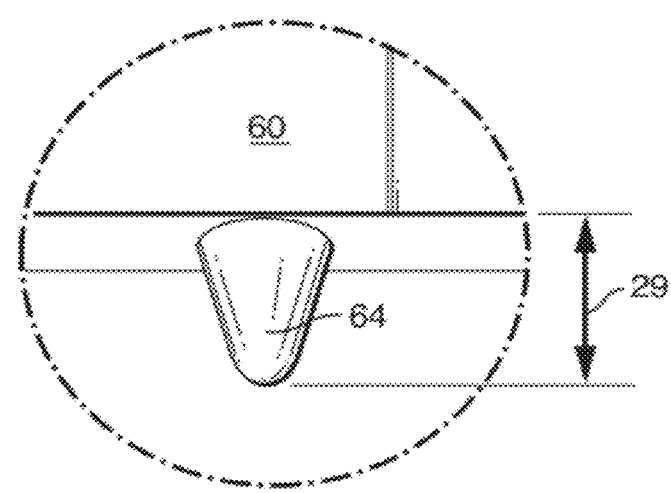
FIG. 14 representatively illustrates an enlarged view of detail A of FIG. 13.
Figure 15:
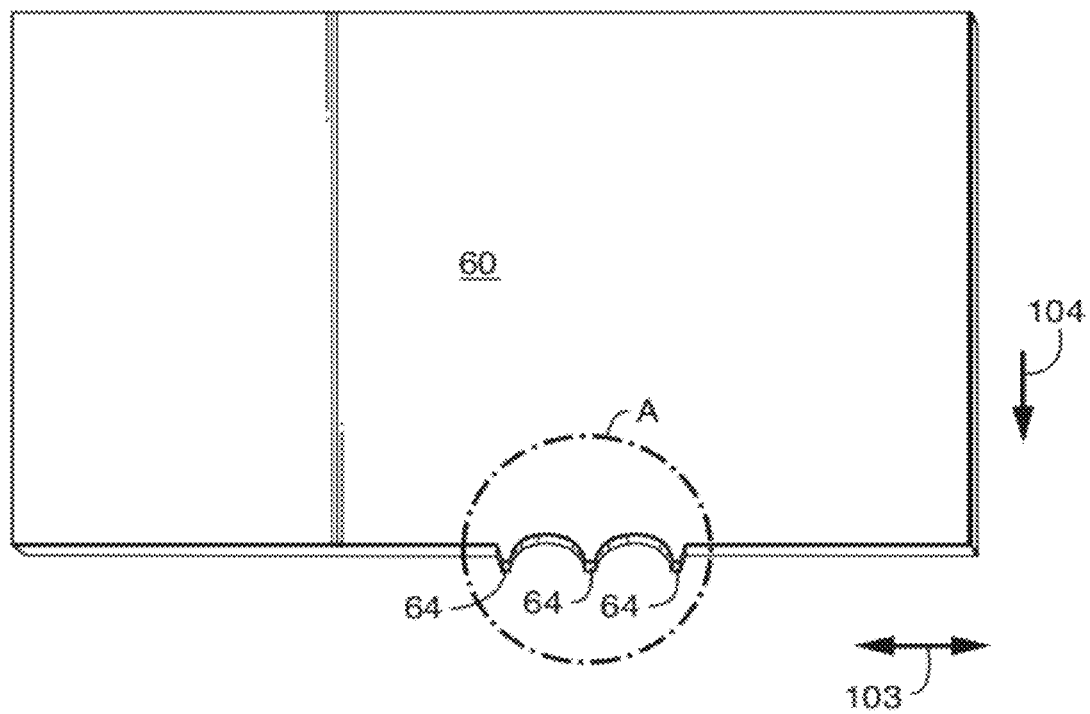
FIG. 15 representatively illustrates a broad side view of another exemplary indentation press jaw of the present invention.
Figure 16:
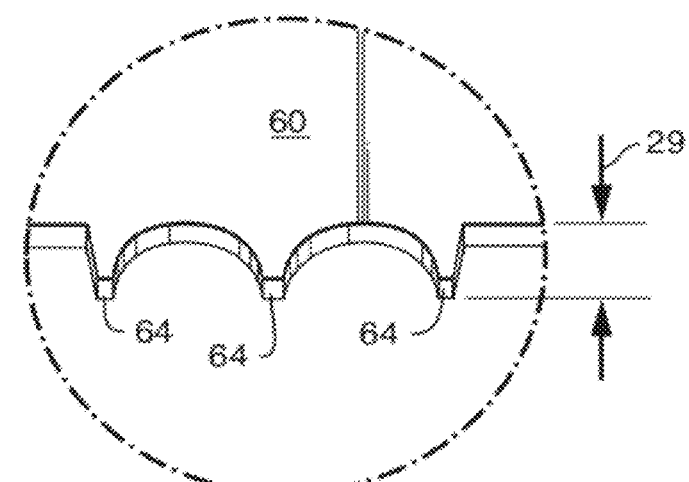
FIG. 16 representatively illustrates an enlarged view of detail A of FIG. 15.

FIG. 9 representatively illustrates the step 14 in the method 13 wherein the absorbent blank 16 is first provided to the mold cavity 68 of the compression unit 19 but before the absorbent blank 16 has been compressed (i.e., an uncompressed configuration). Referring now to FIG. 10, the compression unit 19 of FIG. 9 is illustrated at the peak of compression in the perpendicular direction 104 (i.e., a compressed configuration). Specifically, FIG. 10 illustrates the step 18 in the method 13 wherein the absorbent blank 16 is compressed into a pledget 20. In FIG. 10, the eight indentation press jaws 60 and the eight groove press jaws 62 have moved in the direction 104 that is perpendicular to and/or radially inward towards the longitudinal centerline 102 to compress the pledget 20. The indentation press jaws 60 include one or more discrete projections 64. The discrete projections 64 penetrate the pledget 20 to form the discrete indentations 26 (FIG. 1) which are believed to increase layer integration at these points.

FIGS. 9 and 10 illustrate end views of exemplary indentation press jaws 60. In contrast, FIGS. 11-21 illustrate various broad side views of exemplary indentation press jaws 60 having profiling surfaces 70 and discrete projections 64 extending therefrom. The profiling surfaces 70 are adapted to compress the absorbent blank and provide shape to a portion of the outer surface 27 of the resultant pledget 20 (FIG. 1). Likewise, the discrete projections 64 are adapted to compress the absorbent blank and then penetrate the pledget to form the discrete indentations 26 (FIG. 1) that are believed to integrate the absorbent layers or structure proximate the point of penetration. The point of penetration results in an indentation 26 (FIG. 1).

In various embodiments, the discrete projections 64 may have any suitable shape, dimensions, and/or volume. In some embodiments, the discrete projections 64 may be in the shape of a pyramid, a cone, a cylinder, a cube, an obelisk, or the like, or any combination thereof. For example, the discrete projections 64 may be in the shape of a cone with a relatively pointed apex like illustrated in FIG. 20. In another example, the discrete projections 64 may be in the shape of a cone with a rounded apex like illustrated in FIGS. 13 and 14. In some embodiments, the discrete projections 64 may be in the shape of a pyramid like illustrated in FIGS. 11 and 12. In some embodiments, the discrete projections 64 may have a rectangular shape at the apex with at least one curving side like illustrated in FIGS. 15, 16, 17, and 19.

Figure 17:
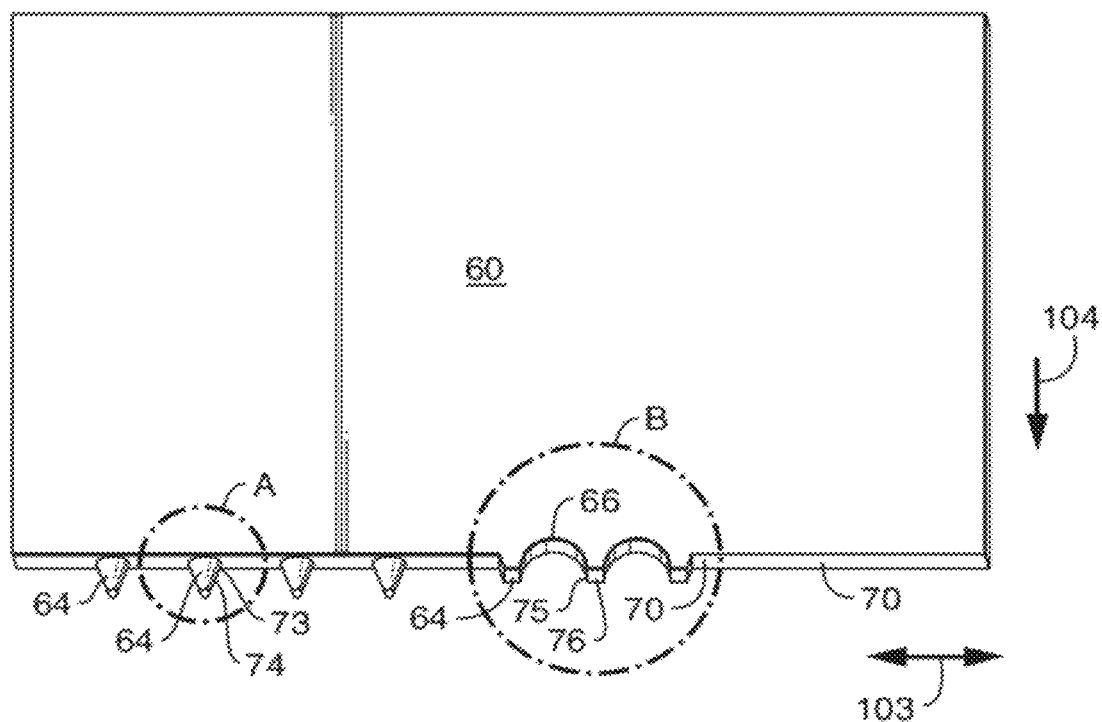
FIG. 17 representatively illustrates a broad side view of another exemplary indentation press jaw of the present invention.
Figure 19:
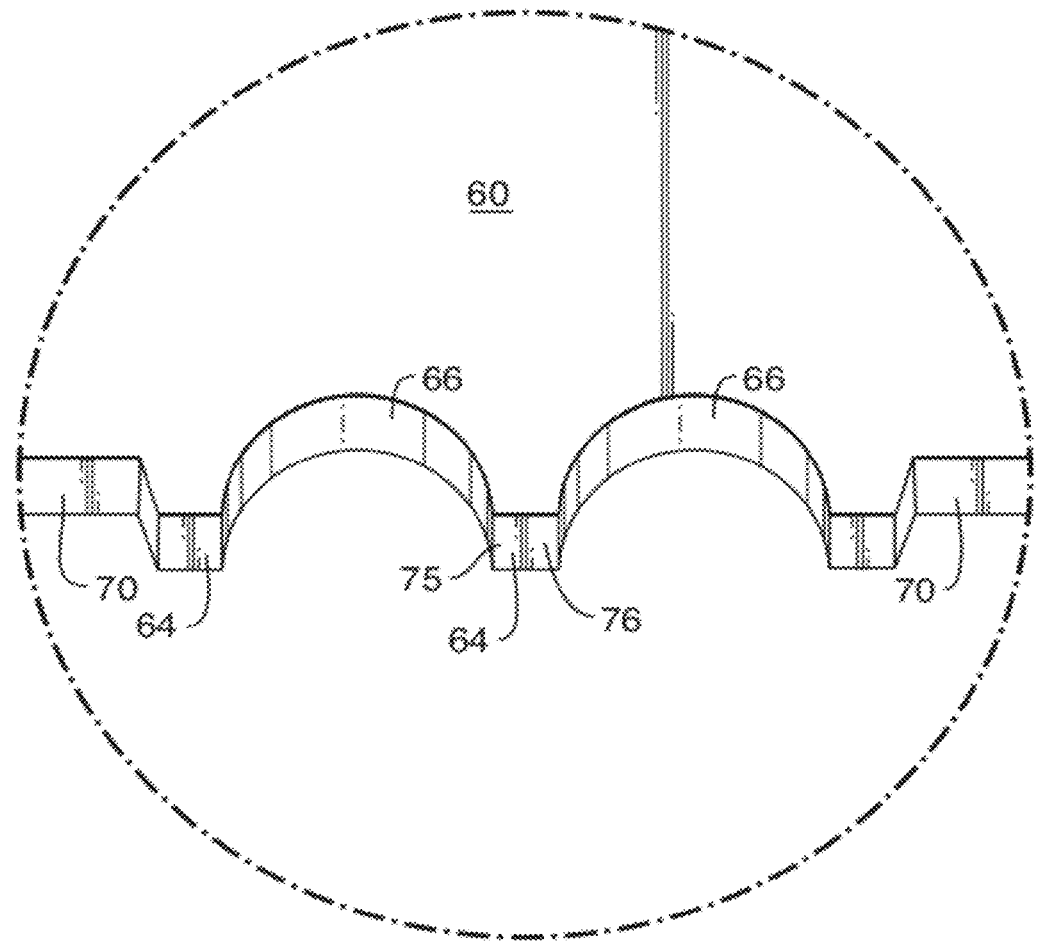
FIG. 19 representatively illustrates an enlarged view of detail B of FIG. 17.

In some embodiments, the indentation press jaws 60 may have a discrete relief 66 like illustrated in FIGS. 17 and 19. The discrete relief 66 extends into the indentation press jaw 60 and may have any suitable shape. For example, as illustrated in FIG. 19, the discrete relief 66 may have an arched shape. In these embodiments, when a plurality of indentation press jaws 60 compress the absorbent blank 16 into the pledget 20, a circumferentially raised ring 46 is formed as illustrated in FIG. 4.

Figure 18:
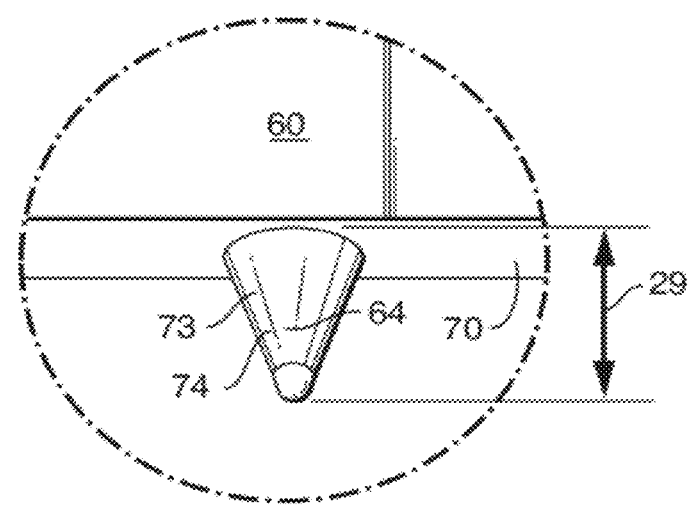
FIG. 18 representatively illustrates an enlarged view of detail A of FIG. 17.

In various embodiments, one or more of the indentation press jaws 60 may include a first discrete projection 73 having a first shape 74 and a second discrete projection 75 having a second shape 76 that is different than the first shape 74. For example, FIG. 17 representatively illustrates a first discrete projection 73 having a first shape 74 wherein the first shape 74 is a cone (FIG. 18). FIG. 17 also representatively illustrates a second discrete projection 75 having a second shape 76, wherein the second shape 76 is more cubic.

In some embodiments, a compression unit may include a first indentation press jaw having a first discrete projection having a first shape. Likewise, the compression unit may include a second indentation press jaw having a second discrete projection having a second shape. In various embodiments, the first shape and the second shape may be the same or may be different. For example, in some embodiments, the first indentation press jaw may include discrete projections having the shape of cones and the second indentation press jaw may include discrete projections having the shape of pyramids.

Figure 20:
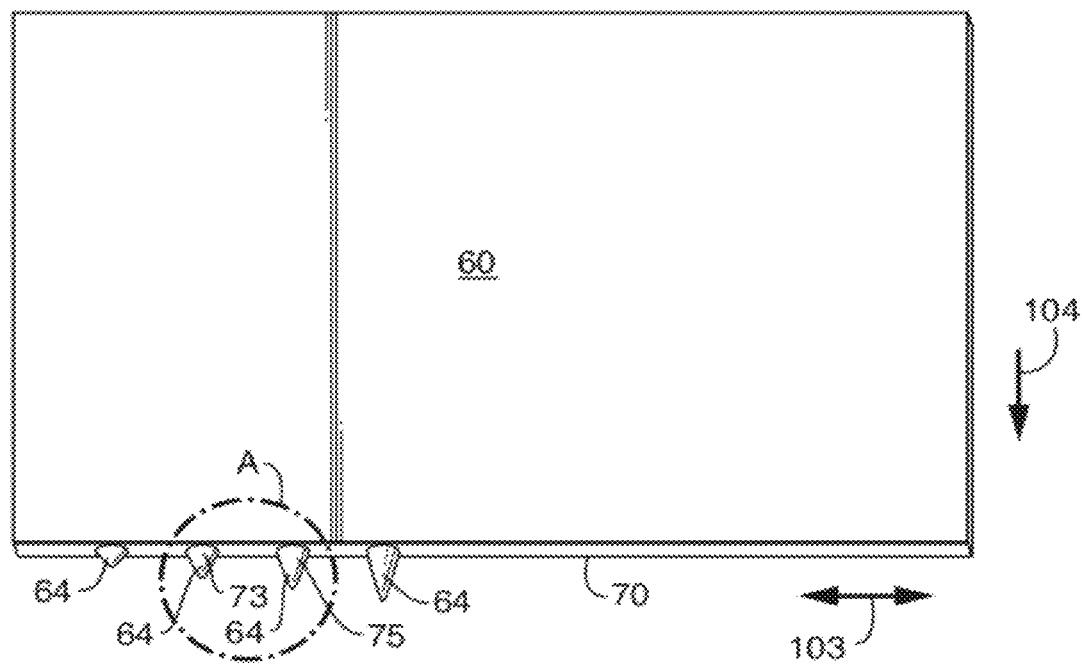
FIG. 20 representatively illustrates a broad side view of another exemplary indentation press jaw of the present invention.
Figure 21:
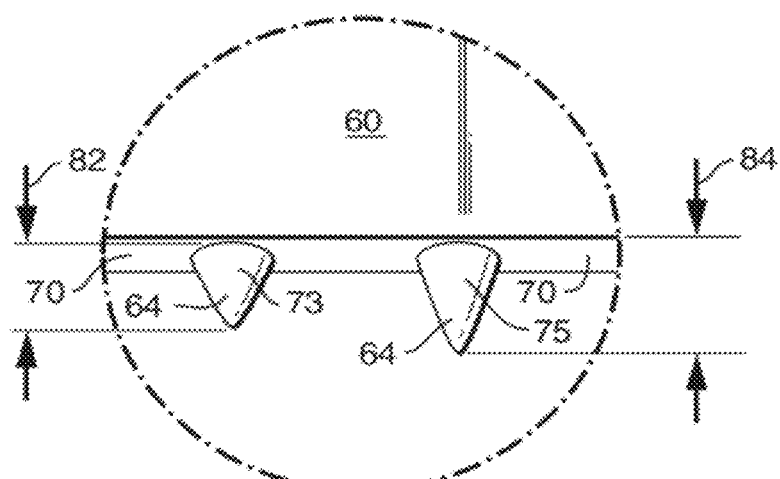
FIG. 21 representatively illustrates an enlarged view of detail A of FIG. 20.

In various embodiments, the discrete projections 64 may extend any suitable distance from the profiling surface 70. For example, referring now to FIGS. 12, 14, 16, and 18, the projections 64 may have an extension dimension 29 of at least 0.5 mm, at least 1 mm, at least 1.5 mm, at least 2 mm, at least 2.5 mm, or at least 3 mm. In various embodiments, one or more indention press jaws 60 may have discrete projections 64 wherein two or more of the discrete projections 64 have the same extension dimension 29 like illustrated in FIGS. 11 and 13. In some embodiments, one or more indentation press jaws 60 may have two or more discrete projections 64 having different extension dimensions 29 like illustrated in FIG. 20. Specifically, FIG. 20 illustrates an indentation press jaw 60 having a profiling surface 70 wherein a first discrete projection 73 has a first extension dimension 82 (FIG. 21) and a second discrete projection 75 has a second extension dimension 84 (FIG. 21). As illustrated, the second extension dimension 84 is greater than the first extension dimension 82.

In some embodiments, a compression unit may include a first indentation press jaw having a first discrete projection having a first extension dimension. Likewise, the compression unit may include a second indentation press jaw having a second discrete projection having a second extension dimension. In various embodiments, the first extension dimension and the second extension dimension may be the same or may be different. For example, in some embodiments, the first indentation press jaw may include discrete projections having an extension dimension that is less than the extension dimension of the discrete projections of the second indentation press jaw.

Because the profiling surfaces 70 of the indentation press jaws 60 define the compressed diameter 22 of the pledget 20 (FIGS. 6 and 8), the extension dimension 29 equals the penetration depth 72 of the discrete projection 64 into the pledget 20. The penetration depth 72 can be defined as a percentage of the compressed diameter 22 of the pledget 20. For example, in various embodiments, the discrete projections 64 may have a penetration depth 72 of at least 20%, at least 30%, at least 40%, or at least 50% of the compressed diameter 22 of the pledget 20. For example, in some embodiments, the compressed diameter 22 may be about 6.6 mm and the extension dimension 29 may be about 2.55 mm such that the penetration depth 72 is 39% of the compressed diameter 22.

In various embodiments, the discrete projections 64 may have a volume of at least 3, at least 4, or at least 5 cubic millimeters. In specific embodiments, the discrete projections 64 may be blunted cones having a base diameter of 2.523 mm and a height of 2.546 mm for a volume of 5.045 cubic millimeters. In various embodiments, the volume and/or the shape of the discrete projections may be selected to provide the desired layer integration. In various embodiments, at least 80%, at least 90%, or at least 95%, or 100% of the volume of the discrete projections 64 may penetrate the compressed pledget 20. Thus, in these embodiments, the displaced volume of absorbent material that initially forms the indentations 26 is at least 80%, at least 90%, at least 95%, or 100% of the volume of the discrete projections 64.

Referring again to FIGS. 1-4, the pledgets 20 defines a first half 36 having an insertion end 38 and a second half 40 having a withdrawal end 42. In some embodiments, the methods of the present invention include penetrating the pledget 20 with discrete projections 64 such that there are more indentations 26 formed in the first half 36 than in the second half 40. For example, FIGS. 1 and 4 representatively illustrate pledgets 20 having more indentations 26 in the first half 36 than in the second half 40. This is believed to be beneficial because the withdrawal string 21 is frequently anchored in the first half 36 of the pledget 20 while extending from the withdrawal end 42 of the second half 40. As such, the withdrawal forces applied are first directed at the first half 36. Thus, creating greater layer integration via the indentations 26 in the first half 36 is believed to counteract the withdrawal forces and help maintain the integrity of the pledget 20. In some embodiments, the first half 36 has at least 25%, at least 50%, or at least 75% more indentations 26 than the second half 40. In some embodiments, all the indentations 26 may be in the first half. In some embodiments, at least 60%, at least 70%, at least 80%, or at least 90% of the indentations 26 may be in the first half 36.

In some embodiments, the methods of the present invention include the step of forming a first circumferentially raised ring 46 around the pledget 20 in the second half 40. In some embodiments, the methods of the present invention include the step of forming a second circumferentially raised ring 48 around the pledget 20 as illustrated in FIG. 4. In various embodiments, the first circumferentially raised ring 46 and the second circumferentially raised ring 48 may be separated by a circumferential groove 50.

In some embodiments, the methods of the present invention include the step of penetrating the pledget 20 to form one or more longitudinal rows 34 of indentations 26. For example, FIGS. 1-4 illustrate pledgets 20 having a plurality of longitudinal rows 34 of indentations 26. In various embodiments, a first row 35 of indentations 26 may be aligned in the circumferential direction 106 with a second row 37 of indentations 26 as illustrated in FIG. 3. In some embodiments, a first row 35 of indentations 26 may be staggered in the circumferential direction 106 with a second row 37 of indentations 26 as illustrated in FIGS. 1, 2, and 4. In various embodiments, the first row 35 of indentations 26 and the second row 37 of indentations 26 may be adjacent rows as illustrated in FIGS. 1-4. In some embodiments, the longitudinal rows of indentations may extend around the circumferential direction 106 of the pledget 20 and may be staggered such that adjacent rows of indentations are not aligned as illustrated in FIGS. 1, 2, and 4.

In various embodiments, the methods of the present invention include the step of forming one or more longitudinal grooves 30 in the absorbent pledgets 20. For example, FIGS. 1-4 illustrate pledgets 20 having a plurality of longitudinal grooves 30. Likewise, the methods of the present invention may include the step of providing a plurality of longitudinal grooves 30 and providing a plurality of longitudinal rows 34 of indentations 26 wherein the longitudinal grooves 30 and the longitudinal rows 34 are alternated in the circumferential direction 106 of the pledget 20 as illustrated in FIGS. 1-4.

The absorbent blanks 16 and ultimately the pledgets 20 of the present invention may include any suitable type and/or combination of absorbent fibers and/or binder fibers. The absorbent fibers may include any suitable absorbent material made from artificial or natural fibers, such as polyester, cellulose, acetate, nylon, polypropylene, rayon, cotton or blends thereof. The absorbent fibers may also include any suitable blend of fibers. For example, the absorbent fibers can be formed from cellulosic fibers, such as cotton and rayon. The absorbent fibers can be 100 wt % cotton, 100 wt % rayon, or a blend of cotton and rayon fibers. In some embodiments, the cellulose fibers may be modified for super-absorbency.

In some embodiments, the absorbent blanks 16 and ultimately the pledgets 20 may include a combination of absorbent fibers and long binder fibers like those taught in U.S. application Ser. No. 13/051,447 to Jackson et al. which was filed on Mar. 18, 2011, and is incorporated herein by reference where not contradictory.

When cotton fibers are used, the cotton fibers should have a staple length of between about 20 millimeters (mm) to about 40 mm. The cotton fibers should generally have a fiber size of between about 15 microns to about 28 microns. The cotton fibers can also be bleached if desired. Bleaching will make the cotton fibers whiter in appearance.

When rayon fibers are present, the rayon fibers should have a staple length of between about 20 mm to about 45 mm. In some embodiments, rayon fibers may have a staple length of 38-42 mm. Suitable rayon fibers may have a denier of between about 1 to about 6. In specific embodiments, the rayon fibers may be viscose rayon, lyocell rayon, or any other suitable rayon or regenerated cellulose.

The rayon fibers may have a circular, bi-lobal, or tri-lobal cross-sectional configuration, or some other cross-sectional configuration known to those skilled in the art. The bi-lobal configuration has a cross-sectional profile which looks like a dogbone while the tri-lobal configuration has a cross-sectional profile which looks like a "Y". The rayon fibers can also be bleached if desired.

In various embodiments, the absorbent blanks may be rolled, stacked, folded, or otherwise manipulated before being compressed into pledgets. For example, suitable menstrual tampons may include "cup" shaped pledgets like those disclosed in U.S. Patent Application Publication 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" type pledgets like those disclosed in U.S. Pat. No. 2,464,310 to Harwood; "M-folded" tampon pledgets like those disclosed in U.S. Pat. No. 6,039,716 to Jessup; "stacked" tampon pledgets like those disclosed in U.S. Patent Application Publication 2008/0132868 to Jorgensen; or "bag" type tampon pledgets like those disclosed in U.S. Pat. No. 3,815,601 to Schaefer.

A suitable method for making "radial wound" pledgets is disclosed in U.S. Pat. No. 4,816,100 to Friese. Suitable methods for making "W-folded" pledgets are disclosed in U.S. Pat. No. 6,740,070 to Agyapong; U.S. Pat. No. 7,677,189 to Kondo; and U.S. Patent Application Publication 2010/0114054 to Mueller. A suitable method for making "cup" pledgets and "stacked" pledgets is disclosed in U.S. Patent Application Publication 2008/0132868 to Jorgensen.

In various embodiments, the tampons of the present invention may also include a cover material disposed over at least a portion of the outer surface. The cover may be beneficial in assuring that the fibers of the pledget do not directly contact the inner walls of a woman's vagina. This minimizes the likelihood that fibers will be left behind in the vagina after the tampon has been removed. The cover may be tucked into the insertion end and/or the withdrawal end so as to substantially or completely surround and enclose the absorbent fibers. The cover can also be constructed from a heat-sealable material to assist in bonding all or portions of it to the pledget, such as by heat and/or pressure.

The optional cover can be formed from a nonwoven material such as a polyolefin, particularly polypropylene or polyethylene. The cover material may be spunbond. In some embodiments, the cover material may be a bonded carded web made of bicomponent fibers (e.g., polyethylene/polyethylene terephthalate sheath core). In some embodiments, the cover material may be a film material made from polypropylene, polyethylene, or a combination of both. For example, in some embodiments, the cover may have three layers made of polyethylene-polypropylene-polyethylene. In some embodiments, the cover material may have apertures having a diameter of 1 mm or less or 0.5 mm or less.

Figure 22:
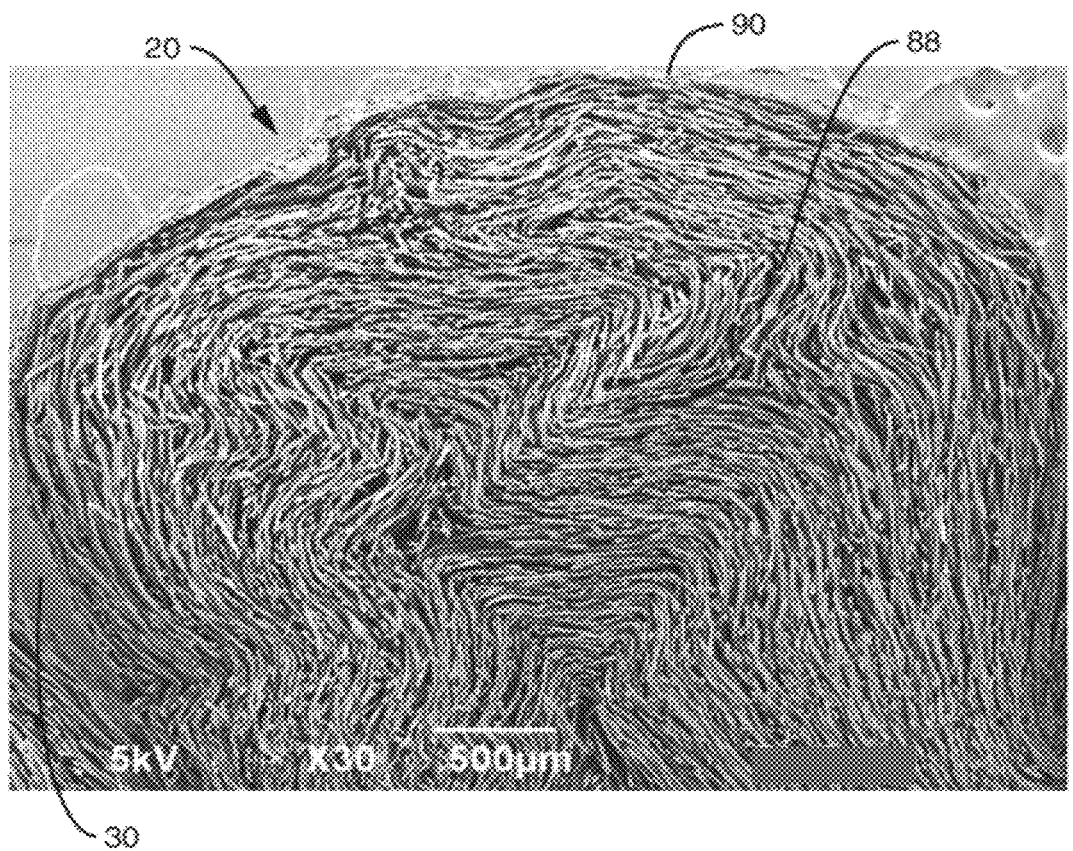
FIG. 22 is a SEM photomicrograph cross-sectional image of a portion of an absorbent pledget without an indentation.

In embodiments that include a cover material, the methods of the present invention may also include the step of penetrating the pledget before or after the cover material has been applied. For example, in some embodiments, the method may further include the step of wrapping the absorbent blank with a cover material before compressing into a pledget. In these embodiments, one or more of the indentations may also include a void space located under the cover material. For example, referring now to FIGS. 22-24, Scanning Electron Microscope (SEM) photomicrographs of cross-sections of various pledgets are reproduced. The SEM photomicrographs were taken of tampons supported in a close-fitting plastic tube while cutting and were taken using 30 times magnification. Referring now to FIG. 22, a cross-sectional view of a portion of a pledget 20 is shown without an indentation. Specifically, FIG. 22 shows a mass of absorbent fibers 88 that are generally aligned in irregular layers and are at least partially surrounded by a cover material 90. FIG. 22 also shows a cross-sectional view of a longitudinal groove 30.

Figure 23:
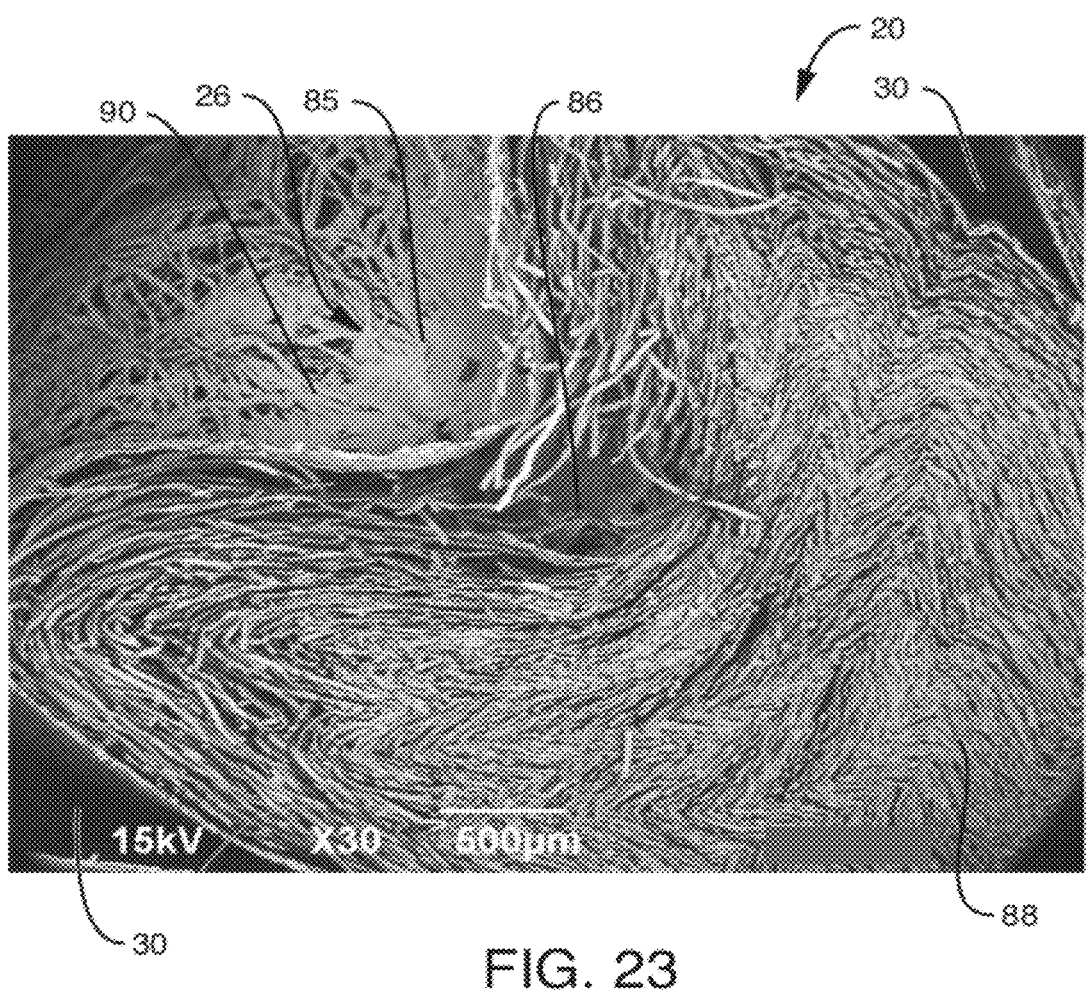
FIG. 23 is a SEM photomicrograph cross-sectional image of a portion of an absorbent pledget containing an indentation.

Referring now to FIG. 23, a cross-sectional view of a portion of a pledget 20 is shown with an indentation 26 and longitudinal grooves 30. The pledget 20 of FIG. 23 was compressed, penetrated, and grooved after the cover material 90 was added. In other words, the cover material 90 and the absorbent fibers 88 were compressed and penetrated at the same time to form the discrete indentation 26. The indentation 26 includes a first void space 85 above the cover material 90 and a second void space 86 below the cover material 90. At the bottom of the second void space 86, the absorbent fibers 88 are highly compressed and at least partially broken.

Figure 24:
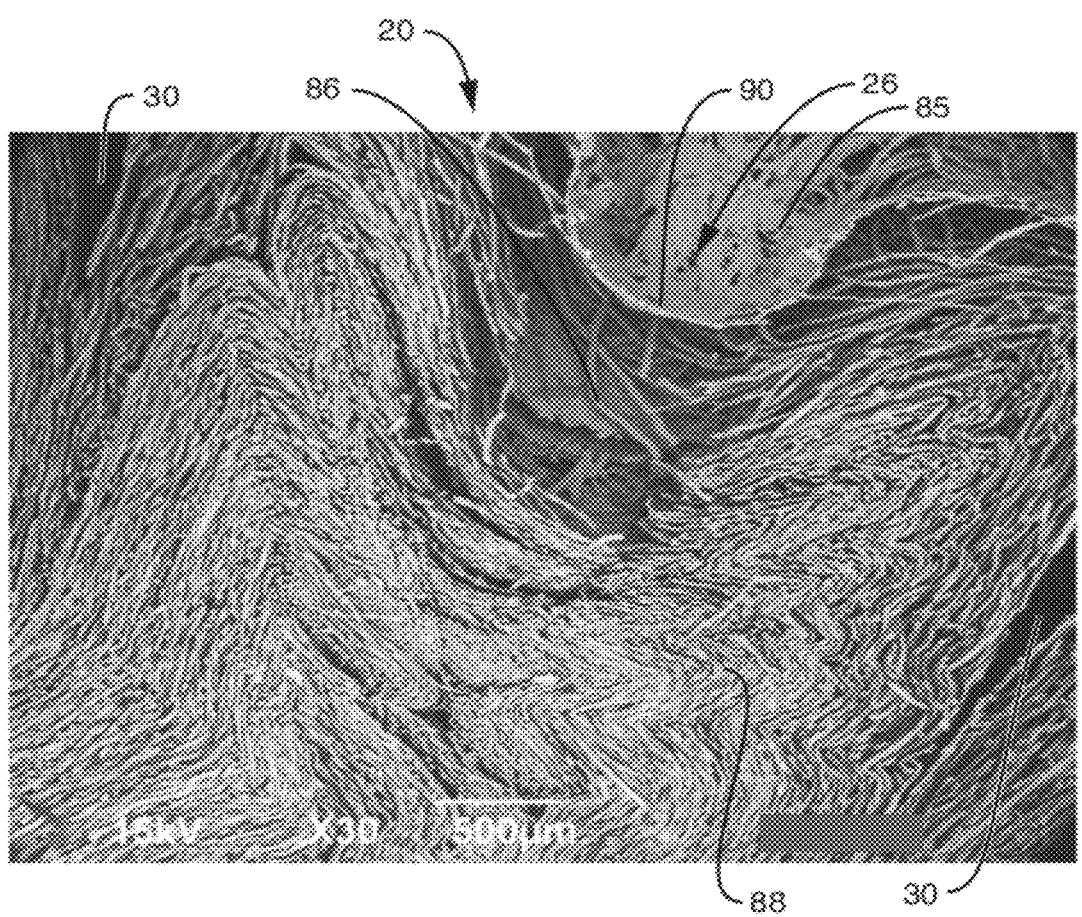
FIG. 24 is a SEM photomicrograph cross-sectional image of a portion of another absorbent pledget containing an indentation.

Referring now to FIG. 24, another cross-sectional view of a portion of a pledget 20 is shown with an indentation 26 and longitudinal grooves 30. Like FIG. 23, the cover material 90 and the absorbent fibers 88 were penetrated at the same time to form the indentation 26. The indentation 26 includes a first void space 85 above the cover material 90 and a second void space 86 below the cover material 90. The absorbent fibers 88 are highly compressed and at least partially broken at the bottom of the indentation 26.

It is believed that this localized (i.e., intermittent) penetration and compression of the absorbent layers displaces absorbent material and creates disruptions to the surface-to-surface interaction between the layers. As such, it is believed that the pledget 20 is better able to withstand withdrawal forces without delaminating, unrolling, unfolding, telescoping, or otherwise structurally degrading. This belief is supported by an experiment wherein a commercially available radially wound tampon with compressed grooves was penetrated to 39% of the compressed diameter of 6.6 mm with 56 discrete projections (8 rows of 7 discrete projections each) having an extension dimension of 2.55 mm and a shape like that illustrated in FIG. 11 to create 56 discrete indentations. This indented tampon was tested against a control tampon with compressed grooves that did not have discrete indentations. The indented tampon was found to have a peak telescoping force that was more than three times the peak telescoping force of the control tampon.

Figure 25:
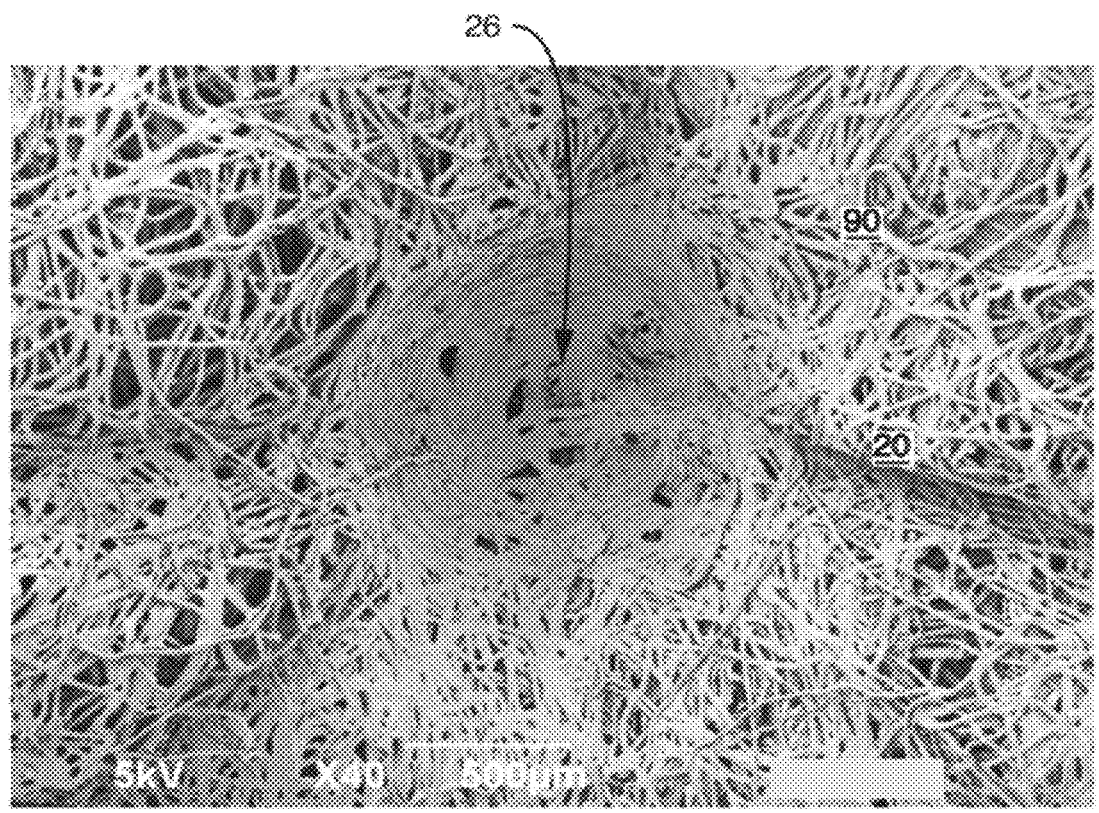
FIG. 25 is a SEM photomicrograph top-view image of an indentation.

In various embodiments, the penetration of the cover and the pledget may rupture the cover material. In other embodiments, the penetration of the cover and the pledget displaces absorbent material under the cover but does not rupture the cover. For example, referring now to FIG. 25, a Scanning Electron Microscope (SEM) photomicrograph shows a top view of a pledget 20 having a cover 90 and an indentation 26. FIG. 25 shows that the cover 90 is highly compressed in the indentation 26 but no ruptures are visible and no underlying absorbent fibers are visible.

In various embodiments, the withdrawal string 21 may be attached to the pledget 20 in any suitable manner. For example, an opening can be formed through the pledget 20 (and cover if provided) so as to provide a means for attaching a withdrawal string 21. In various embodiments, the withdrawal string 21 may be attached to the absorbent blank 16 before or after it is compressed into the pledget 20. The withdrawal string 21 may be attached to the pledget 20 and then looped upon itself. A knot 31 can then be formed near the free ends of the withdrawal string 21 to assure that the string 21 does not separate from the pledget 20. The knot 31 also serves to prevent fraying of the withdrawal string 21 and to provide a place or point where a woman can grasp the withdrawal string 21 when she is ready to remove the tampon 10 from her vagina.

The withdrawal string 21 can be constructed from various types of threads or ribbons. A thread or ribbon may be made from 100 percent cotton fibers and/or other materials in whole or part. In some embodiments, the withdrawal string 21 may be 67% polyethylene terephthalate and 33% rayon. The withdrawal string 21 may be bonded to the absorbent blank and/or the pledget with or without tying. The withdrawal string 21 may have any suitable length and/or the withdrawal string 21 can be dyed and/or treated with an anti-wicking agent, such as wax, before being secured to the pledget 20.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A method of integrating a tampon comprising
providing an absorbent blank with a longitudinal centerline,
compressing the absorbent blank into a pledget having a compressed diameter and a plurality at longitudinal grooves,
penetrating the pledget in a direction perpendicular to the longitudinal centerline to form a plurality of longitudinal rows of indentations, wherein the longitudinal grooves and the longitudinal rows of indentations are circumferentially alternating and wherein a first row of indentations is staggered in a circumferential direction as compared with a second row of indentations.

2. The method of claim 1 wherein the method includes the step of at least partially wrapping the absorbent blank with a cover before compressing the absorbent blank and the cover to form the pledget and penetrating the pledget and the cover in the perpendicular direction to a compressed depth of at least 30% of the compressed diameter to form the rows of indentations.

3. The method of claim 1 wherein pledget defines a first half having an insertion end and a second half having a withdrawal end and the method further includes penetrating the pledget in the perpendicular direction to form 25% more indentations in the first half than the second half.

4. The method of claim 3 wherein the method further includes the step of forming a first circumferentially raised ring around the pledget in the second half.

5. The method of claim 4 wherein the method further includes the step of forming a second circumferentially raised ring around the pledget, wherein the first circumferentially raised ring and the second circumferentially raised ring are separated by a circumferential groove.

6. The method of claim 1 wherein the pledget is penetrated to a compressed depth of at least 30% of the compressed diameter.

7. The method of claim 1 wherein the rows of indentations and the longitudinal grooves are formed in a simile compression unit.

8. The method of claim 1 wherein the pledget defines a first half and a second half and wherein the method further includes forming more indentations in the first half than in the second half.

9. The method or claim 1 wherein the pledget is penetrated to a compressed depth of at least 20% of the compressed diameter.

* * * * *